(12) United States Patent
Bernhard et al.

(10) Patent No.: US 11,103,647 B2
(45) Date of Patent: Aug. 31, 2021

(54) INJECTION DEVICE COMPRISING A COVER CAP AND A SYSTEM FOR PREVENTING THE COVER CAP FROM BEING REMOUNTED

(71) Applicant: Ypsomed AG, Burgdorf (CH)

(72) Inventors: Mario Bernhard, Burgdorf (CH); Markus Tschirren, Burgdorf (CH); Tashi-Panso Tsching, Olten (CH)

(73) Assignee: Ypsomed AG, Burgdorf (CH)

(*) Notice: Subject to any disclaimer, the term of this patent is extended or adjusted under 35 U.S.C. 154(b) by 258 days.

(21) Appl. No.: 16/257,711

(22) Filed: Jan. 25, 2019

(65) Prior Publication Data

US 2019/0151561 A1 May 23, 2019

Related U.S. Application Data

(63) Continuation of application No. PCT/CH2017/000061, filed on Jun. 21, 2017.

(30) Foreign Application Priority Data

Jul. 26, 2016 (CH) .................................. 00959/16

(51) Int. Cl.
*A61M 5/32* (2006.01)
*A61M 5/20* (2006.01)
*A61M 5/50* (2006.01)

(52) U.S. Cl.
CPC ........ *A61M 5/3202* (2013.01); *A61M 5/2033* (2013.01); *A61M 5/3213* (2013.01);
(Continued)

(58) Field of Classification Search
CPC .............. A61M 5/3202; A61M 5/2033; A61M 5/3213; A61M 5/50; A61M 5/3204;
(Continued)

(56) References Cited

U.S. PATENT DOCUMENTS 4,571,242 A 2/1986 Klein et al.
2016/0325044 A1 11/2016 Tschirren et al.

FOREIGN PATENT DOCUMENTS

EP 2745866 A1 6/2014
WO 2008113199 A1 9/2008
(Continued)

OTHER PUBLICATIONS

PCT, "International Preliminary Report on Patentability", Application No. PCT/CH2017/000061, dated Jan. 29, 2019, 15 pages.
(Continued)

*Primary Examiner* — Theodore J Stigell
*Assistant Examiner* — Rachel T. Smith
(74) *Attorney, Agent, or Firm* — Dorsey & Whitney LLP

(57) ABSTRACT

An injection device for distributing a liquid product, in particular a medicament, includes: a) a housing with a longitudinal axis (L) and a product container, in particular a syringe, provided in the housing, the product container including a displaceable plunger, where the plunger can be displaced along the longitudinal axis (L) in a distal direction using a propulsion member to distribute the product contained in the product container; b) a cover cap which is mounted on the distal end of the housing and which can be removed from the housing; and c) a mechanism which prevents the cover cap from being remounted on the distal end of the housing.

12 Claims, 5 Drawing Sheets

(52) U.S. Cl.
CPC .............. *A61M 5/50* (2013.01); *A61M 5/3204* (2013.01); *A61M 2005/2013* (2013.01); *A61M 2005/2073* (2013.01)

(58) Field of Classification Search
CPC .. A61M 2005/2013; A61M 2005/2073; A61M 5/5086; A61M 5/3287; A61M 5/31513; A61M 5/347; A61M 2005/3289; A61M 2005/2474; A61M 5/3293; A61M 5/24
See application file for complete search history.

(56) References Cited

FOREIGN PATENT DOCUMENTS

| | | | |
|---|---|---|---|
| WO | 2011047298 A2 | 4/2011 | |
| WO | WO-2016135250 A1 * | 9/2016 | .......... A61M 5/3202 |

OTHER PUBLICATIONS

PCT, "International Search Report and Written Opinion", Application No. PCT/CH2017/000061, dated Sep. 19, 2017, 19 pages.

* cited by examiner

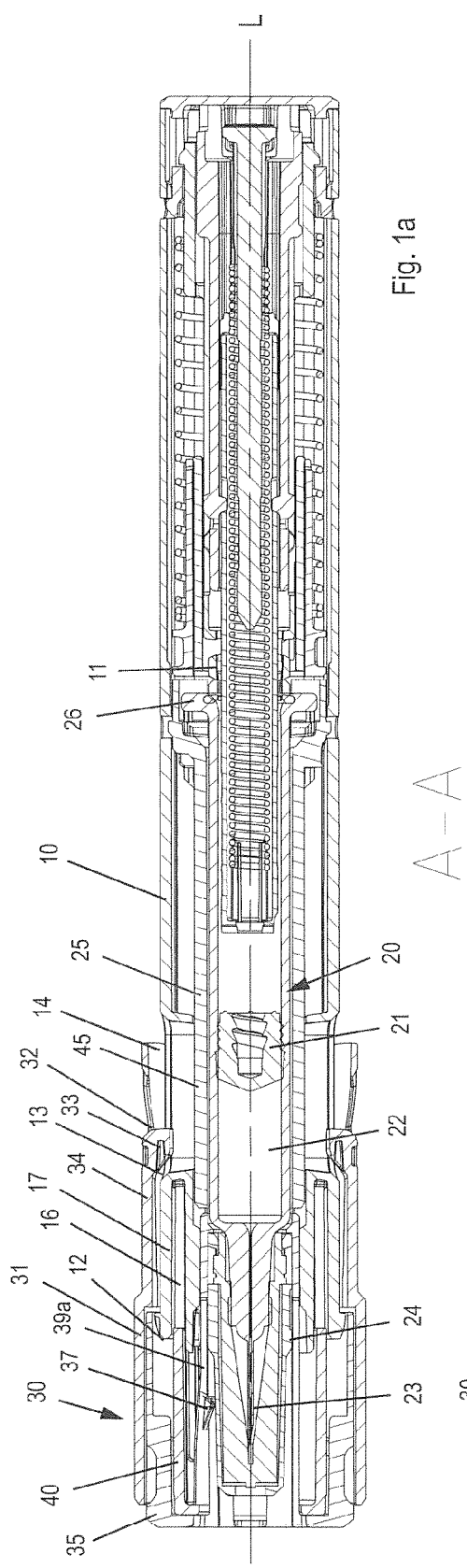
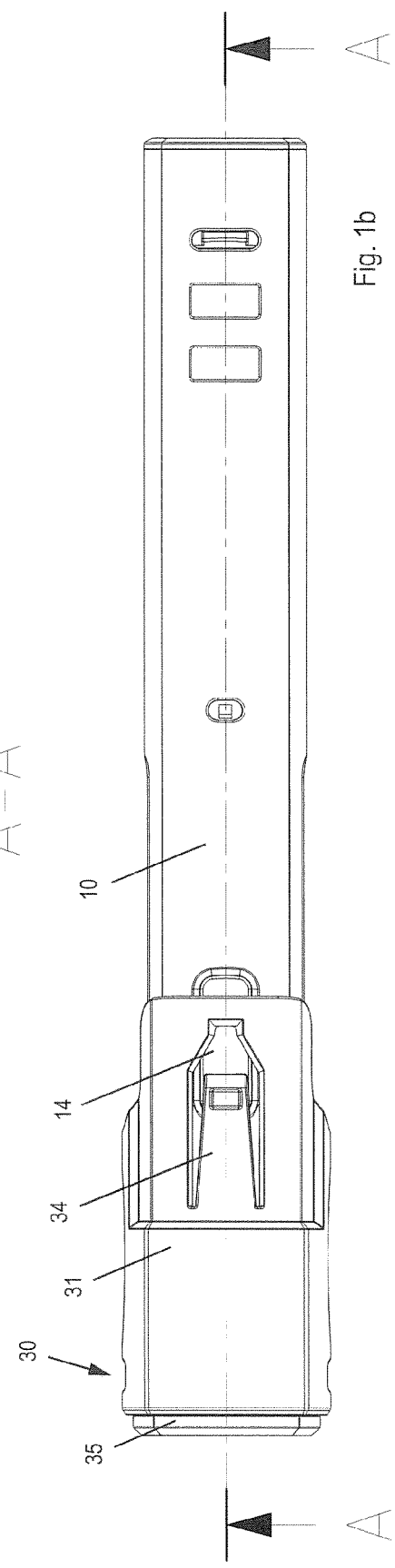
Fig. 1a
Fig. 1b

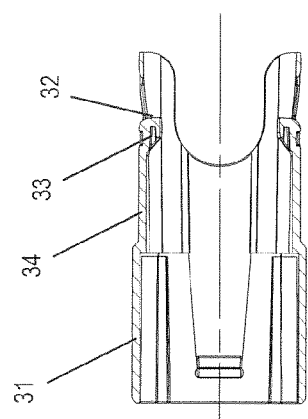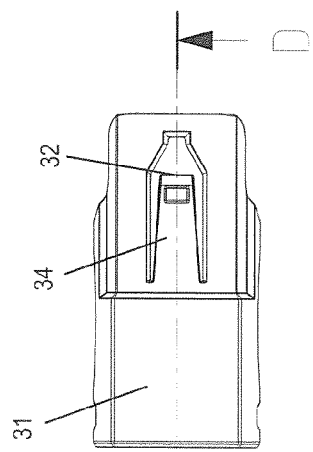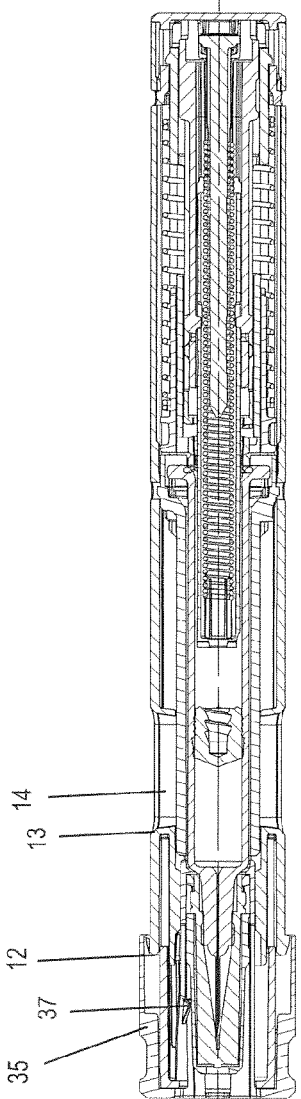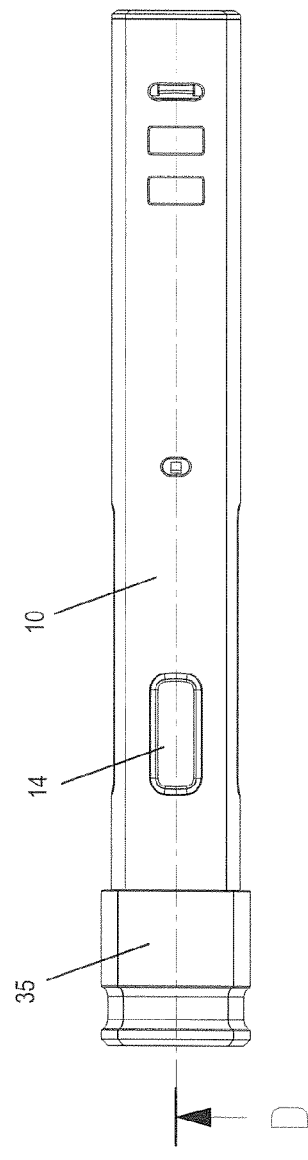
Fig. 2a
Fig. 2b

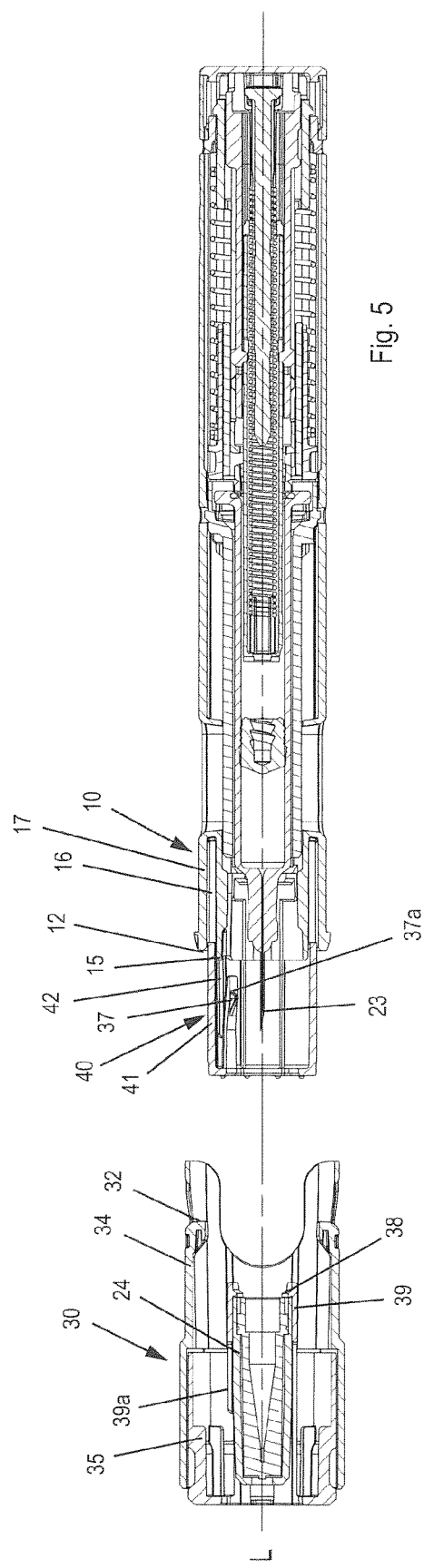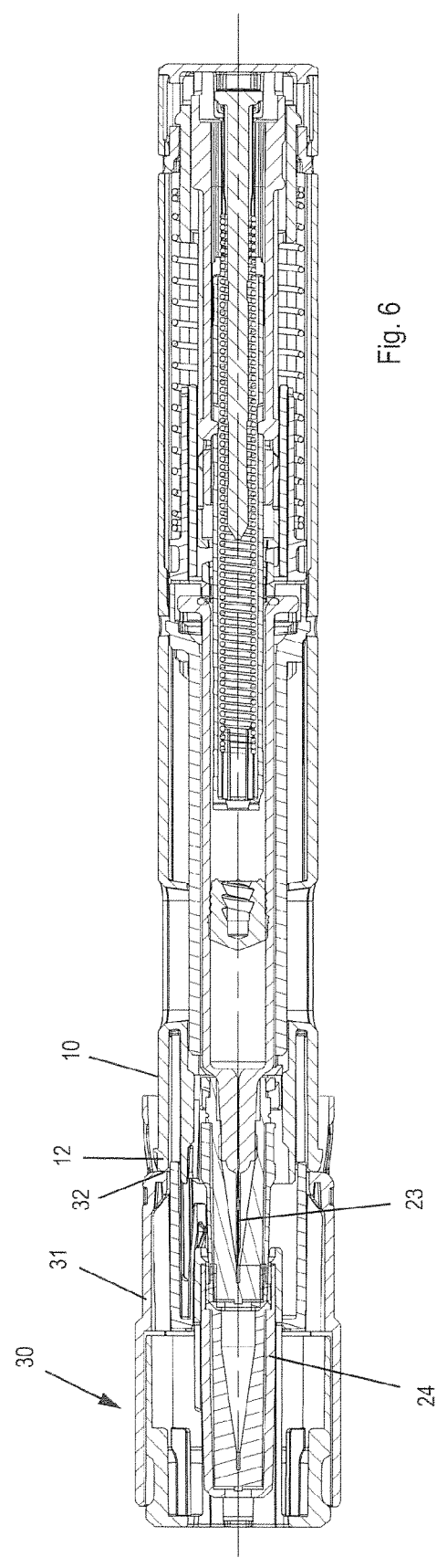

INJECTION DEVICE COMPRISING A COVER CAP AND A SYSTEM FOR PREVENTING THE COVER CAP FROM BEING REMOUNTED

CROSS-REFERENCE TO RELATED APPLICATIONS

This application is a continuation of International Application No. PCT/CH2017/000061 filed Jun. 21, 2017, which claims priority to Swiss Application No. 00959/16 filed Jul. 26, 2016, the entire contents of all of which are incorporated by reference herein in their entirety.

FIELD OF THE INVENTION

The invention relates to an injection device for discharging or administering a fluid product, in particular, a medicine. In particular, the invention relates to a mechanism for the injection device which prevents or blocks a cover cap from being remounted after it has been removed from the distal end of the injection device.

BACKGROUND

The term "medicine" here includes any flowable medicinal formulation, for example, comprising a fluid, a solution, a gel, or a fine suspension that contains one or more active medicinal ingredients that is suitable for controlled administration through a means, e.g., a cannula or hollow needle. A medicine can be a compound with a single active ingredient or a pre-mixed or co-formulated compound with multiple active ingredients from a single container. Medicines include drugs such as peptides (e.g., insulins, medicines containing insulin, GLP preparations, GLP-derived preparations or GLP analog preparations), proteins and hormones, biologically obtained or active ingredients, active ingredients on the basis of hormones or genes, nutritional formulations, enzymes, and other substances both in solid (suspended) or fluid form, but also polysaccharides, vaccines, DNA or RNA or oligonucleotides, antibodies or parts of antibodies and suitable base substances, additives, and carrier substances.

SUMMARY OF THE INVENTION

From the prior art, injection devices are known in which a syringe, which is also called a pre-filled syringe, is arranged. The pre-filled syringe can be arranged in a housing of the injection device in a displaceable or non-displaceable manner. It is known to mount a cover cap that is taken off or removed from the housing before the injection device is used for administering the product. Often, the needle is surrounded by a needle protective cap that is mounted on the syringe and is kept sterile with respect to the surroundings. From the state of the art, constructions are known in which the needle protective cap is connected to the cover cap by means of at least one engagement element, whereby the needle protective cap is also removed when the cover cap is removed, in that the engagement element carries along the needle protective cap. However, it is also conceivable that first the cover cap is removed from the housing, and the needle protective cap is removed from the product container in a separate step.

In constructions in which the needle protective cap is removed together with the cover cap, the cover cap can be remounted together with the needle protective sleeve in injection devices from the prior art, for example, if the user of the injection device has decided that he or she does not yet want to use the injection device. By removing the needle protective sleeve and remounting it, a user can mistakenly assume that the needle is still sterile, especially if a long time passes and the user can no longer remember that he or she already removed the needle protective sleeve.

From the prior art, constructions of injection devices are also known, in particular, auto-injectors, which have a release safety device that prevents the unintentional movement of a release element constructed, for example, as a needle protective sleeve, in the proximal direction, when the cover cap is mounted on the housing. Remounting the cover cap can have the result that the mechanism of the release safety device is manipulated such that the mechanism also prevents the movement of the release element in the proximal direction when the cover cap is removed and therefore actually makes the movement of the release element possible in the proximal direction. An auto-injector with a release safety device is described, for example, in EP 2 745 866 A1, whose release element has a preferably spring-mounted locking means, wherein the locking means can be deflected by the cover cap into a locking position in which the locking means is opposite a stop formed by the auto-injector, wherein, in a release position that the locking means assumes, the locking means can be moved past the stop when the cover cap is removed. By remounting or improper remounting of the cover cap, it can happen that the locking means is pressed by the cover cap or a section of the cover cap into the locking position and is held permanently in the storage state of the auto-injector, whereby—depending on the material and/or with increasing storage time—a permanent deformation of the locking means is created, so that the locking means no longer moves from its locking position even when the cover cap is removed, whereby the release element is blocked against moving into the release position, even if the cover cap has been removed from the housing.

Disclosed is an injection device that reduces the risk of faulty applications in connection with the removal of a cover cap and, in particular, remounting of the cover cap on the housing of the injection device.

The injection device according to claim 1 provides such benefits. Advantageous refinements are given from the dependent claims, the description, and the figures.

The invention starts from an injection device, e.g., an auto-injector, for discharging a fluid product, in particular, a medicine. The injection device comprises a housing that preferably has an elongated and/or sleeve-shape construction. The housing can be used, for example, by the user of the device for gripping with one hand and/or for holding a product container and/or a mechanism for discharging the product. In the housing there is a product container. The product container can be, in particular, a syringe that has a syringe body on whose distal end an injection needle is arranged in a fixed manner. The preferably cylindrical syringe body surrounds a plunger that can move with reference to the syringe body and is moved toward the distal end for discharging the product, whereby the fluid product, in particular, medicine, arranged between the plunger and the injection needle is discharged from the product container though the injection needle. The syringe body can have, on its proximal, i.e., rear end or end opposite the injection needle, a flange that can be constructed as and called a finger flange. A syringe with such a construction is available as a standard syringe, so that a specially adapted syringe does not need to be developed for the injection device. The plunger contacts the inner diameter of the syringe body in a sealing and displaceable manner.

The preferably elongated, sleeve-shaped housing forms the longitudinal axis of the injection device. The housing is preferably cylindrical, for example, circular-cylindrical, polygonal-cylindrical, or in general, non-round in cross section, whereby, in contrast to a circular-cylindrical housing, the injection device can be prevented from rolling away. The product container is arranged in the housing. For example, the container can be arranged to be displaceable in the housing, i.e., displaceable relative to the housing in the distal direction for automatic injection, so that the needle tip emerges from an opening at the distal end of the injection device and can be automatically inserted into the patient. Optionally, for such a device, the needle tip can be moved into the distal end of the device after successful discharge of the product, in particular, the product container can be moved in the proximal direction relative to the housing.

In constructions, the product container can be held in the housing so that it is non-displaceable along the longitudinal axis, in particular, holds the product container fixed axially and is connected, in particular, latched, with the housing in an axially fixed manner. In particular, the needle tip can extend in the distal direction past the distal end of the housing. In this way, the needle can be moved to the injection position by means of moving the housing toward the patient.

The injection device can have a driving element, e.g., a plunger rod, wherein the driving element can be displaced in the distal direction along the longitudinal axis for discharging the product contained in the product container. For example, the driving element can be displaced manually, i.e., by the muscle force of the user, in the distal direction. Alternatively, the driving element can be moved by an energy storage device, e.g., a spring, a pressure accumulator, or a gas generator for discharging the product contained in the product container along the longitudinal axis in the distal direction. The different possibilities for displacing the driving element in the distal direction for discharging the product are numerous and well known.

The injection device comprises a cover cap that is mounted on the distal end of the housing, in particular, in the delivery state of the auto-injector. The cover cap is removable from the housing, in particular, can be pulled off or rotated off, in particular, unscrewed. For removing the cover cap, with reference to the housing, at least one movement component is performed along the longitudinal axis in the distal direction with reference to the housing. For preparing the injection device for proper use, the cover cap is removed from the housing. In embodiments with a release element that is displaced for initiating the injection and/or discharge of the product in the proximal direction relative to the housing, the cover cap can be mounted, for example, on the housing and can surround the distal end of the release element, wherein it prevents or blocks, in particular, access to the distal end of the release element. If the cover cap is removed from the housing, access to the release element is enabled, so that it can be placed on the injection point.

The cover cap can be connected, e.g., snapped together, with the housing with a positive-fit and/or non-positive-fit connection in its position, in particular, completely mounted on the injection device or housing. For example, the cover cap can have an engagement element and the housing can have an engagement mating element that engage with each other when the cover cap is mounted, in particular, completely on the housing. Obviously, this engagement is detachable by the movement of the cover cap, in order to allow the cover cap to be removed from the housing.

According to the invention, the injection device has a mechanism that prevents or blocks the cover cap from being remounted on the distal end of the housing. Remounting is understood to mean a mounting process in which the cover cap has been removed from the housing from its position mounted, in particular, completely on the distal end of the housing and is then placed on the housing again, in particular, completely mounted.

In constructions of the injection device, the product container can have an injection needle that is connected with it, in particular, in non-detachable manner or alternatively in a detachable manner. The injection needle can be surrounded by a needle protective cap that can be mounted on the product container, in particular, a needle holding section that surrounds the proximal end of the needle, in particular, encapsulates it in a non-detachable manner. The needle holding section can attach to the cylindrical syringe body in the distal direction. The needle protective cap can be mounted, for example, in a friction fit or positive fit or in a combination friction or positive fit, on the product container, in particular, on or to the needle holding section. The needle protective cap surrounds the injection needle and seals it in a sterile manner with reference to the surroundings. The needle protective cap can be constructed, for example, as a so-called "soft needle shield" or "rigid needle shield," as is known from the prior art. A soft needle shield comprises or consists of a preferably cap-shaped part formed from an elastomer, for example, based on a synthetic or natural rubber, which surrounds the needle. The soft needle shield has, on its outer circumference, a soft surface formed, e.g., from a synthetic or natural rubber-like material. A rigid needle shield usually has multiple parts, in particular, an elastomer cap-shaped inner part and a sleeve-shaped or cap-shaped outer part made from a solid or more solid, i.e., non-elastomer plastic, which holds the inner part and is connected to it in an essentially non-detachable manner. The outer sleeve-shaped or cap-shaped part surrounds the inner cap-shaped part and is connected to the inner cap, for example, in a non-detachable manner, so that the outer and inner cap form a unit. The outer part can be formed from a harder plastic than the inner part. The outer part can be formed, for example, from polyethylene, polystyrene, polypropylene, or another suitable plastic. The inner part can be formed, for example, from synthetic rubber or natural rubber or another suitable, in particular, elastomer material.

In refinements, the cover cap can be connected to the needle protective cap such that the removal of the cover cap also removes the needle protective cap from the product container. The cover cap that can be coupled with one or more engagement elements, can be connected to the needle protective cap by means of the at least one engagement element so that the removal of the cover cap from the injection device or its housing causes the removal of the needle protective cap from the product container. For example, at least one part of the movement or the entire movement of the cover cap can be transferred to the engagement element in the distal direction, for example, so that the engagement element is carried along by the cover cap, so that the engagement element pulls the needle protective cap from the product container, in particular, the needle holding section.

The at least one engagement element can be formed, for example, by the cover cap or by a, for example, sleeve-shaped removal element that is arranged so that it is non-displaceable or is limitedly displaceable along the longitudinal axis on the cover cap, so that the removal element is carried along by the cover cap when the cover cap is removed, in particular, along the longitudinal axis L.

The at least one engagement element can connect to the needle protective cap or can engage in the needle protective cap, so that the needle protective cap is removed from the product container when the cover cap is pulled away by the engagement element. For example, the cylindrical section of the product container can taper on its distal end and transition, for example, into the needle holding section. Between this tapering end and the proximal end of the needle protective cap, for example, a gap can be formed in which the engagement element is arranged. Alternatively, the engagement element can engage in the outer circumferential surface of the needle protective cap. The engagement element can already be attached to or engaged in the product container in the delivery state or it can be brought into engagement only during the removal of the cover cap from the housing.

The cover cap and the needle protective cap can form one unit during and/or after the removal of the cover cap from the housing, such that the needle protective cap is held in the cover cap and cannot be detached from the cover cap or cannot be detached without additional means. The cover cap and the needle protective cap thus form one manageable unit.

Because the needle protective cap is pulled away from the injection needle when the cover cap is removed from the housing in these constructions, the injection needle can come into contact with the surrounding atmosphere, whereby it is no longer considered sterile. Remounting or re-attaching the cover cap on or to the housing could give the appearance that the needle is still sterile. By means of the mechanism according to the invention that prevents the cover cap from being remounted, in particular, completely remounted, on the distal end of the housing, for example, so that the needle protective sleeve, in particular, its engagement element snapped together with the housing, in particular, the engagement mating element of the housing, prevents that the complete remounting causes it to appear to a user that the needle is still sterile. This reduces the risk of incorrect application of the injection device.

As an alternative or addition to the previously mentioned embodiments, the injection device can have, in particular, a sleeve-shaped release element that extends in its starting position past the distal end of the housing and can be moved, when the cover cap is removed from the housing, in a proximal direction from the starting position into a release position for releasing the discharge relative to the housing, and is blocked against movement into the release position when the cover cap is arranged on the housing. Blocking is understood, in particular, as not just the simple prevention of access to the sleeve-shaped release element, but instead a block is formed with two parts contacting each other. The release element is used primarily for releasing the discharge of the product or an optional injection sequence. Optionally, the release element can be used as a needle protective sleeve and designed or constructed as such. The release element that forms the distal end of the injection device when the cover cap is removed can have an opening for the injection needle, wherein the injection needle can pass through the opening. The release element can be arranged in its starting position with reference to the needle tip so that the release element, in particular, the needle protective sleeve, extends in the distal direction past the needle tip or the needle tip extends in the distal direction past the distal end of the release element. The release element is displaceable relative to the housing in the proximal direction by an actuation travel distance from its starting position into an actuated position, in particular, actuation position, in particular, displaceable in the housing, so that the needle extends from or farther from the distal end or through the opening of the release element. For example, the release element can be displaced by a needle protection travel distance from the release position relative to the housing in the distal direction into a needle protection position, in which the distal end of the release element, in particular, the needle protective sleeve, extends in the distal direction past the needle tip, in order to reduce the risk of injury due to an exposed needle tip after successful use of the device or after successful discharge of the product.

The release element can be displaced in the proximal direction, for example, against the force of a spring, that can be designated, for example, as a non-return spring or needle protection spring, wherein the spring can move the release element in the distal direction from the position in which a locking means locks the movement of the release element in the proximal direction or can move the release element from the release position in distal direction, for example, into the needle protection position.

The, in particular, sleeve-shaped release element that extends in its starting position past the distal end of the housing is movable for the release of the discharge relative to the housing from the starting position in the proximal direction into the release position, when the cover cap is removed from the housing. The release element is coupled with a drive mechanism that is preferably surrounded by the housing such that the drive mechanism releases the discharge of the product or optionally an injection sequence, when the release element is in its release position or reaches the release position.

In refinements, the release element can be blocked against movement into the release position when the cover cap is arranged on the housing. For example, the release element cannot be moved in the proximal direction at all, or can be moved only by an amount that is less than the release travel distance, i.e., the distance that the release element travels when moving from the starting position into the release position.

In an especially preferred way, the present invention can be used in the auto-injector from EP 2 745 866 A1, wherein the content of that publication is incorporated by reference into the present application.

The release element is blocked against movement into the release position when the cover cap is arranged on the housing. For example, the release element cannot be moved in the proximal direction at all, or can be moved only by an amount that is less than the release travel distance, i.e., the distance that the release element travels when moving from the starting position into the release position.

For example, the injection device can have a driving element that acts on the plunger at least during the discharge of the product, in particular, contacts the plunger, and a discharge spring that acts on the driving element as it is supported, for example, in particular, with its distal end on the driving element. The driving element can have, for example, a sleeve-shaped construction and can form a shoulder that is arranged, for example, in the area of the distal end of the driving element, on which the distal end of the discharge spring can be supported. The discharge spring can be arranged preferably within the, for example, sleeve-shaped driving element. The discharge spring is preferably a coil spring acting as a compression spring, which is formed, for example, from metal. The discharge spring can be pretensioned so much, in particular, in the delivery state of the auto-injector, that it or the energy stored in it is enough to essentially completely discharge the product from the product container by displacing the driving element by a discharge travel distance. By displacing the driving element by the discharge travel distance, the plunger is also displaced. If there is a spacing between the plunger and the driving element in the delivery state, the discharge travel distance of the plunger is smaller than the discharge travel distance of the driving element, which is preferred, because the plunger remains unloaded until use, which prevents unintentional, premature discharge of the product. However, it is also basically possible that the driving element contacts the plunger in the delivery state and not only during the discharge of the product. If the driving element is already in contact with the plunger in the delivery state, the discharge travel distance of the plunger corresponds to the discharge travel distance of the driving element. The proximal end of the discharge spring can be supported on the housing or a housing-fixed element, in particular, also an element that is only temporarily axially fixed to the housing.

In refinements, the release element can have or form, for example, articulated or preferably resiliently-mounted locking means. The release element can have a sleeve-shaped main body on which the locking means is arranged in an articulated or resiliently-mounted manner, in particular, is formed integrally with the main body. The locking means can be deflected by the cover cap into a locking position in which the locking means is opposite a stop formed by the injection device, in particular, in alignment with the stop. In its release position that the locking means assumes when the cover cap is removed, the locking means can be moved past the stop, i.e., not in alignment with the stop. Thus, the cover cap can form an actuator that presses or can move the locking means into the release position, in particular, relative to the main body, when the cover cap is arranged on the housing, in particular, arranged completely on the housing. When the cover cap is removed from the housing, this actuator is missing, whereby the locking means is no longer pressed or can no longer be pressed into its locking position. Preferably it is achieved in this way that, with the removal of the cover cap from the housing, the user of the auto-injector simultaneously also removes the release element for moving from the starting position into the release position. If the cover cap is arranged on the housing, the release element is blocked or locked against movements from the release position. By means of the locking means, the auto-injector can no longer be released by the mass inertia of the release element that occurs with strong vibrations.

In particular, an actuator surface that presses the locking means into the locking position can be arranged with respect to the locking means so that the cover cap, in particular, the actuator surface and/or the holding surface, deflects the locking means into its locking position only when the release element is moved from its starting position into the proximal direction, whereby it is guaranteed that the locking means moves into the locking position only when, with the cover cap mounted, the release means is moved from its starting position in the proximal direction, for example, in the event of vibrations, which might be caused, for example, by dropping the injection device onto the floor.

With such an embodiment, under some circumstances, the effect can occur that, when the cover cap is remounted, the locking means is deflected into its locking position and is held in the locking position by the cover cap, for example, by its holding surface. In this way, depending on the material of the locking means and the duration of the deflection, a permanent deformation of the locking means in its locking position can be the result, whereby the locking means no longer moves from the locking position when the cap is removed. By means of the mechanism according to the invention, which prevents the remounting of the cover cap on the distal end of the housing, the locking means may also be prevented from being moved unintentionally into its locking position as remounting of the cover cap is not possible.

In refinements, the mechanism or the injection device can have an axial stop and an axial mating stop, wherein at least one of the axial stop and axial mating stop is brought into a position by the removal of the cover cap, in which the remounting of the cover cap on the distal end of the housing is prevented, in that the axial stop and the axial mating stop contact each other. In other words, the axial stop and the axial mating stop contact each other before the cover cap is mounted on the housing or completely on the housing if an attempt is made to attach the cover cap again to the housing. In particular, at least one of the axial stop and axial mating stop can be deformed during the removal, in particular, elastically deformed, and therefore brought into a position in which the remounting of the cover cap on the distal end of the housing is prevented. An axial stop or axial mating stop is understood to be a structure, e.g., a surface that has a stop surface that is active in the direction of the longitudinal axis.

The axial stop can be formed by the housing or an element supported on the housing at least in the proximal direction. The element supported at least in the proximal direction can be axially fixed or limitedly axially movable along the longitudinal axis L, wherein at least the movement in the proximal direction with reference to the housing is blocked or can be blocked, so that a force acting on the axial stop can be transferred via the element into the housing.

The axial mating stop can be formed by the cover cap or an element supported on the cover cap at least in the distal direction. The element supported on the cover cap at least in the distal direction can be connected to the cover cap axially fixed along the longitudinal axis, in particular, snapped together or connected in a positive fit or limitedly movable with reference to the cover cap, wherein it is preferred that the element can be supported on the cover cap at least in the distal direction, whereby a force exerted on the axial stop is transferred via the element to the cover cap.

For example, the cover cap can have a cover cap base body that is connected, for example, to the housing with a non-positive fit and/or positive fit connection when the cover cap is mounted completely on the housing, especially when the engagement element of the cover cap base body and the engagement mating element of the housing engage with each other. The cover cap can have the cover cap base body and an outer sleeve that is connected, in particular, snapped together, with the cover cap base body at least axially fixed, preferably rotationally locked and axially fixed, and forms the axial mating stop. The outer sleeve can be, for example, pushed on the cover cap of the auto-injector from EP 2 745 866 A1 corresponding to the cover cap base body as a retrofit element. For this purpose, the outer sleeve can be pushed, e.g., via the distal or proximal end of the injection device, over the cover cap or the cover cap base body, whereby the outer sleeve latches or snaps together with the cover cap base body.

In refinements, the axial stop can be arranged in a spring-like, i.e., elastically pliant, manner, in particular, it can be formed by or on the housing and can spring from a deflected position into a locking position with or during the removal of the cover cap from the housing. In the locking position, the axial stop prevents the remounting of the cover cap on the distal end of the housing, in that the axial stop and the axial mating stop contact each other.

Alternatively or additionally, the axial mating stop can be arranged in a resiliently-mounted manner, in particular, on the cover cap or the outer sleeve connected to the cover cap base body, and can spring from a deflected position into a locking position with or during the removal of the cover cap from the housing. In its locking position, the axial mating stop prevents the remounting of the cover cap on the distal end of the housing, in that the axial stop and the axial mating stop contact each other.

In particular, the axial stop and the axial mating stop can be in axial alignment, i.e., in alignment along the longitudinal axis, if there is an attempt to remount the cover cap on the housing.

For example, the cover cap could be placed in one or more discrete rotational positions with respect to the housing, and in all of the different rotational positions (e.g. four rotational positions), one of the mentioned axial mating stops and one of the mentioned axial stops are arranged in alignment along the longitudinal axis, whereby remounting the cover cap is prevented.

For example, the arrangement of the axial stop or the axial mating stop can be constructed so that the axial stop or the axial mating stop springs from the deflected position transversely, in particular, essentially radial to the longitudinal axis, or in the circumferential direction about the longitudinal axis into the locking position. For example, the axial stop and/or the axial mating stop can each be arranged in a resiliently-mounted manner by means of a flexible arm, in particular, with the housing, with an element supported on the housing at least in the proximal direction or on the cover cap or an element supported on the cover cap at least in the distal direction.

For example, the housing can have an actuation or a transmission surface that deflects the axial stop during the removal of the cover cap from the housing from a starting position into its deflected position in a spring-like manner. The actuation or transmission surface can be arranged, for example, so that the axial mating stop—as described above—is deflected somewhat radial to the longitudinal axis or in the circumferential direction about the longitudinal axis, in particular, has a resiliently-mounted design. From this deflected position, the axial mating stop can then spring—as described above—into the locking position. The axial mating stop or an extension that forms the axial mating stop can then slide along the actuation or transmission surface during the removal of the cover cap. The actuation or transmission surface can be arranged inclined, for example, with respect to the longitudinal axis, so that the axial mating stop or the extension can be deflected in a spring-like manner from the starting position into its deflected position.

For example, the housing can have, on its outer periphery, a recess in which an extension or the extension that forms the axial mating stop engages in its starting position, wherein the distal end of the recess can form the transmission surface. The recess can be, for example, an opening through the housing and can be simultaneously used as a window for monitoring the product container. If the axial mating stop is spring mounted, e.g., by means of the arm, the spring-mounted attachment or the arm can be released from tension when the axial mating stop or the extension forming the axial mating stop is in its starting position or engages in the recess. The advantage here is that the attachment or the arm is tensioned only during the removal of the cover cap from the housing, so that it is guaranteed that the axial mating stop springs into its locking position.

In generally preferred constructions, the axial mating stop can be arranged proximal to the axial stop when the cover cap is arranged on the housing, in particular, is arranged completely on the housing. By removing the cover cap, the axial mating stop can be moved along the longitudinal axis past the axial stop. When the cover cap is removed from the housing, the axial mating stop can be located, for example, distal to the axial stop.

In one alternative construction, the injection device can have a rotating sleeve that is supported so that it can rotate, in particular, on and preferably relative to the housing about the longitudinal axis of the injection device and on which the axial stop is formed. In particular, the housing can surround the rotating sleeve. The rotating sleeve is preferably axially fixed but could also be supported such that it is limitedly displaceable on the housing along the longitudinal axis. It is preferred that the rotating sleeve can be supported axially fixed on the housing in the proximal direction. The cover cap or a part or section of the cover cap can slide on the rotating sleeve during the removal of the cover cap from the housing, and the rotating sleeve can rotate about the longitudinal axis, whereby the axial stop that is formed on the rotating sleeve is carried along accordingly with the rotating sleeve about the longitudinal axis, i.e., is rotated into a locking position. In the locking position, the axial stop prevents the remounting of the cover cap on the distal end of the housing, such that the axial stop and the axial mating stop contact each other.

BRIEF DESCRIPTION OF THE DRAWINGS

The invention was described with reference to several preferred constructions and examples. In the following, an especially preferred construction will be described with reference to figures. Features disclosed here advantageously refine the invention individually and in any combination of features, for example, also with one or more features of the preceding description. Shown are:

FIGS. 1a and 1b, an injection device in completely assembled state, wherein FIG. 1a is a section view along the line A-A from FIG. 1b, FIGS. 2a and 2b, the injection device from FIGS. 1a and 1b, wherein an outer sleeve is shown in a position before it is connected to a cover cap base body of a cover cap of the injection device, wherein FIG. 2a is a section view along the line D-D from FIG. 2b, FIG. 3, a section view including a detail view of the injection device from FIGS. 1a and 1b during the removal of the cover cap from a housing of the injection device, FIG. 4, a cross section through the housing of the injection device, FIG. 5, a section view of the injection device from FIGS. 1a and 1b, wherein the cover cap is removed from the housing, and wherein FIG. 6, a section view of the injection device from FIG. 5, during an attempt to remount the cover cap on the housing, and FIGS. 7a and 7b, section detailed views of an alternative construction of an injection device with a rotatable sleeve with the cover cap connected (FIG. 7a) and removed (FIG. 7b).

DETAILED DESCRIPTION

Figure 3:
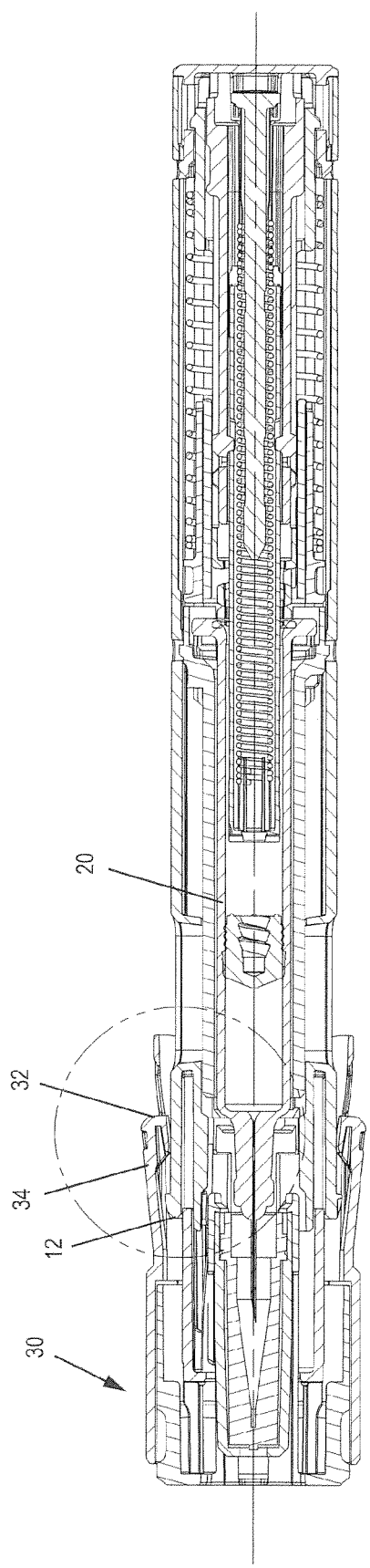
Figure 4:
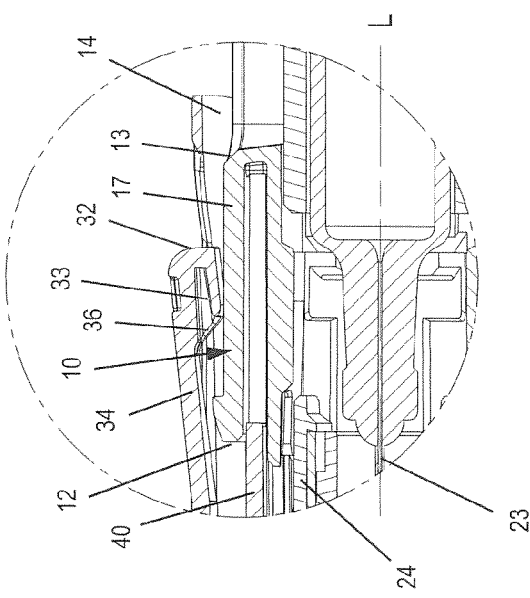

The injection device has a sleeve-shaped, elongated housing 10 with a longitudinal axis L. The injection device shown in the figures corresponds to the auto-injector from EP 2 745 866 A1, but also with the mechanism according to the invention, which prevents the remounting of the cover cap 30. The drive mechanism housed in the rear part is known to someone skilled in the art and can be constructed, for example, as disclosed in EP 2 745 866 A1 or WO 2008/113199 A1, but is not limited to these constructions. Instead, the mechanism could also be used in injection devices in which a needle protective cap 24 is removed with the cover cap 30 and would also be reattached with the remounting of the cover cap 30.

On the distal end of the injection device, in its delivery state (FIGS. 1a, 1b), there is a cover cap 30 that is mounted on the housing 10, for example, with a non-positive or positive fit connection and that is pulled off or rotated off and removed before the auto-injector is used.

In the housing 10 there is a product container 20 in the form of a syringe, displaceable or non-displaceable, for example, with respect to the housing 10, along the longitudinal axis L. The product container 20 has a sleeve-shaped product container section 25 that is designated below as a syringe body and surrounds a plunger 21 that contacts the inner periphery of the syringe body in a sealing manner. The syringe body has, on its distal end, an injection needle 23 that is connected, in particular, in a non-detachable manner to the syringe body and whose distal end is formed by the needle tip. Between the injection needle 23 and the plunger 21 there is a fluid product, in particular, a medicine, within the syringe body, wherein the fluid product is discharged from the product container 20 through the hollow injection needle 23 by displacing the plunger 21 in a discharge direction, i.e., in the distal direction or toward the injection needle 23. The syringe body has, on its proximal end, a so-called finger flange 26 that extends radially outward past the outer periphery of the cylindrical syringe body.

The product container 20 is held in a product container holder 45, which is designated as syringe holder, such that it is secured against moving along the longitudinal axis L in the distal direction relative to the syringe holder. The syringe holder can be connected with a positive fit to the housing 10, in particular, latched together, or can be displaceable relative to the housing 10 along the longitudinal axis L, depending on the construction of the injection device. If the syringe holder is latched with the housing 10, the housing 10 can have recesses for this purpose, in which latching elements that are formed on the syringe holder engage. The syringe holder has at least one inward extending shoulder on which a tapering section of the product container 20 that is arranged distal to the cylindrical syringe body is supported.

The injection device has, on its distal end, a sleeve-shaped release element 40, in particular, needle protective sleeve, which extends in its starting position (e.g., FIG. 5) past the distal end of the housing 10. The release element 40 is completely surrounded by the cover cap when the cover cap 30 is mounted. The release element 40 has a spring-mounted locking means 37 that has a tongue-like or arm-like construction. The elongated locking means 37 extends approximately parallel to the longitudinal axis L and points in the proximal direction with its free end. With its other end, it is integrally connected by means of a spring-mounted section to the release element 40, in particular, a sleeve-shaped main body of the release element 40, in particular, with its distal end. The free end of the locking means 37 forms a contact surface 37a for a stop 15 that is formed by the housing 10. The contact surface 37a points in the proximal direction, wherein the stop surface 15 points in the distal direction. The locking means 37 has a cam that extends toward the longitudinal axis L. The cam is arranged between the free end and the resiliently-mounted section of the locking means 37. The release element 40 has a sleeve-shaped section 41, between which and the locking means 37, a first gap 42 is formed. The housing 10 has, for example, a sleeve-shaped section 17, wherein, between the, for example, sleeve-shaped section 17 of the housing 10 and the stop 15, in particular, a housing section that forms the stop 15, a second gap 16 is formed.

The release element 40 is displaceable in the proximal direction relative to the housing 10, wherein the sleeve-shaped section 41 of the release element 40 is displaced or can be displaced into the second gap 16 and the stop 15, in particular, the housing section, is displaced or can be displaced into the first gap 42.

By moving the release element 40 in the distal direction into a release position, the product discharge or an injection procedure can be triggered in a known way.

In FIGS. 1a and 1b, the cover cap 30 is located in its position mounted on the housing 10. The cover cap 30 forms a holding surface 39a that is arranged proximal to the cam when the release element 40 is in its starting position (FIGS. 1a and 1b). Distal to the holding surface 39a, the cover cap 30 has a recess for the cam, so that the locking means 37 is located by its spring-mounted arrangement in a release position or a position outside of its locking position, wherein the cam is arranged in this recess. The contact surface 37a is here outside of axial alignment along the longitudinal axis L with the stop 15.

If the injection device is, for example, accidentally dropped onto the floor, under some circumstances the release element 40 can be moved relative to the housing 10 in the proximal direction due to its mass inertia. To prevent the release element 40 from moving into its release position, which would have the result that the product could be unintentionally discharged, the movement of the release element 40 into its release position is prevented, in that the locking means 37, in particular, the contact surface 37a contacts the stop 15.

If the release element 40 is moved from its starting position (FIGS. 1a and 1b) relative to the housing 10 in the proximal direction with a mounted cover cap 30, the locking means 37 is deflected from its release position (FIGS. 1a and 1b) into the locking position. The cover cap 30 here has an actuation or transmission surface on which the cam, in particular, an inclined transmission surface of the cam, slides. In this way, the cam and thus also the locking means 37 are deflected in a spring-like manner, in particular, away from the longitudinal axis L. The holding surface 39a that points away from the longitudinal axis L, i.e., outward, on which the cam then contacts, holds the locking means 37 in its locking position. In the locking position, the contact surface 37a is in axial alignment along the longitudinal axis L with the stop 15. In this way it is realized that the contact surface 37a contacts the stop 15 and thus blocks movement of the release element 40 into its release position. In this way it is preferably realized that unintentional release of the auto-injector is prevented as long as the cover cap 30 is mounted on the housing 10.

For preparing the administration of the product, the cover cap 30 is removed from the housing 10. By removing the cover cap 30, the needle protective cap 24 that covers the injection needle 23 is also removed from the product container 20. In the starting or delivery state of the injection device (FIGS. 1a and 1b), for example, when the cover cap 30 is arranged on the injection device and has not yet been removed, the injection needle 23 is covered by the needle protective cap 24 that is constructed in the shown example as a so-called "rigid needle shield," alternatively as a "soft needle shield," which are known to someone skilled in the art, in order to protect the injection needle 23 from contamination and to keep the injection needle 23 and the medicine sterile. The needle protective cap 24 is arranged on a needle holding section of the syringe body, wherein the tapering section of the syringe body is located between the needle holding section and the cylindrical section of the syringe body. The shoulder of the syringe holder is arranged between the syringe body and the proximal end of the needle protective cap 24, in particular, so that a gap—although also minimal—is created between the needle protective cap 24 and the shoulder, in order to prevent the shoulder exerting a force on the needle protective cap 24, whereby, for example, the sterility of the injection needle 24 or of the fluid product could be endangered. The cover cap 30 is snapped together with the housing 10 or the needle protective sleeve 40 in a detachable manner, wherein this snap-together connection is released when the cover cap 30 is removed from the housing 10 or the release element 40. The snap-together connection between the housing 10 and the cover cap 30 has, for example, a snap-together hook that has a snapper engaging in a gap between the syringe body, in particular, its tapering region, and the proximal end of the needle protective cap 24. If the cover cap 30 is removed from the housing 10, the snapper engages in the proximal end of the needle protective cap 24, whereby the needle protective cap 24 is detached from the product container 20 and is removed from the housing 10 together with the cover cap 30. Alternatively, other mechanisms can be used that connect the cover cap 30 to the needle protective cap 24 such that the removal of the cover cap 30 from the housing 10 also removes the needle protective cap 24 from the product container 20.

In FIG. 5, the front part of the injection device is shown, wherein the cover cap 30 is removed together with the needle protective cap 24. In this way, the injection device is prepared for administration. For administration, the distal end of the release element 40 is placed on the desired injection point of the patient. The housing 10 is pressed by the user toward the injection point, wherein the release element 40 is moved in the proximal direction relative to the housing 10. Because the cover cap 30 is removed, the locking means 37 is no longer deflected in the locking position. The locking means 37 is located in its release position. The release element 40 thus can be displaced into its release position, wherein the contact surface 37a is moved past the stop 15, because the contact surface 37a is not in axial alignment along the longitudinal axis L with the stop 15.

In the not-shown release position, the injection needle 23 extends past the distal end of the release element 40, in particular, by a measure that corresponds to the desired injection depth. In the starting position (FIG. 5), the injection needle 23 is surrounded by the preferably sleeve-shaped release element 40. In particular, the release element 40 extends in the distal direction past the distal end of the injection needle 23 when the release element 40 is located in its starting position.

After successful discharge of the product, a spring tensioned, for example, by the movement of the release element 40 in the proximal direction can move the release element 40 relative to the housing 10 in the distal direction, in order to assume a needle protective position (not shown) in which the distal end of the release element 40 extends past the distal end of the injection needle 23. In the needle protective position, the release element 40 is preferably latched with the housing 10, so that it is no longer displaceable in the proximal direction or is at least no longer displaceable far enough that the distal end of the injection needle 23 extends from the distal end of the needle protective sleeve 40.

Figure 7A:
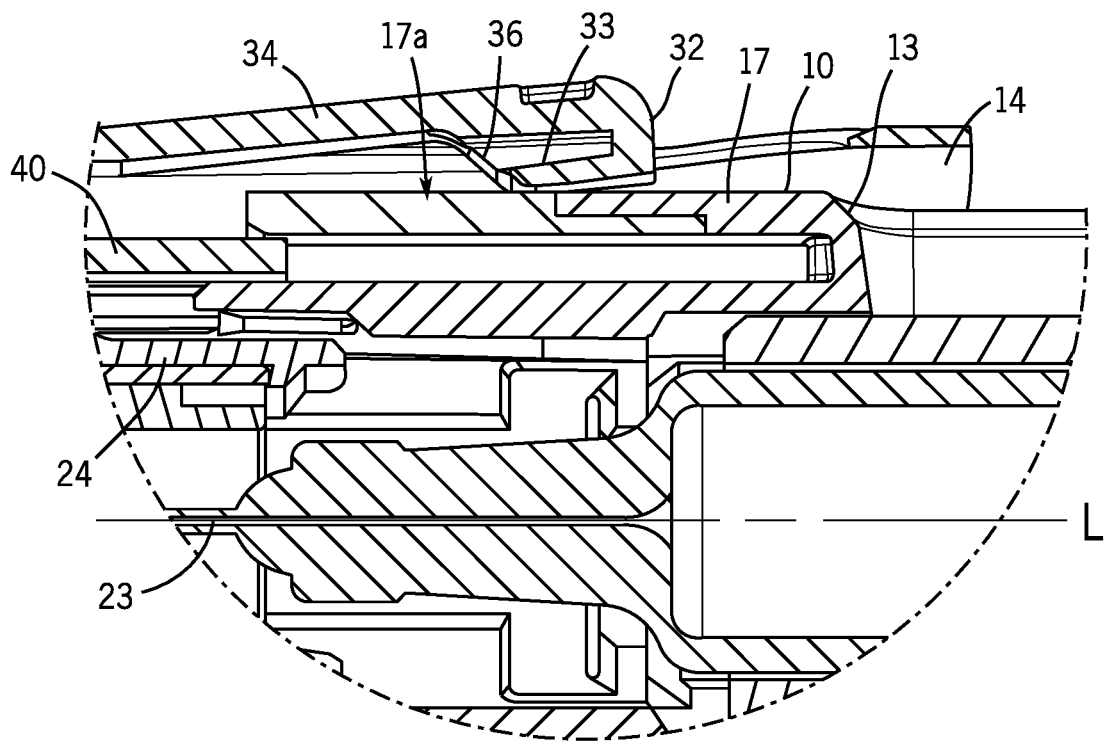
Figure 7B:
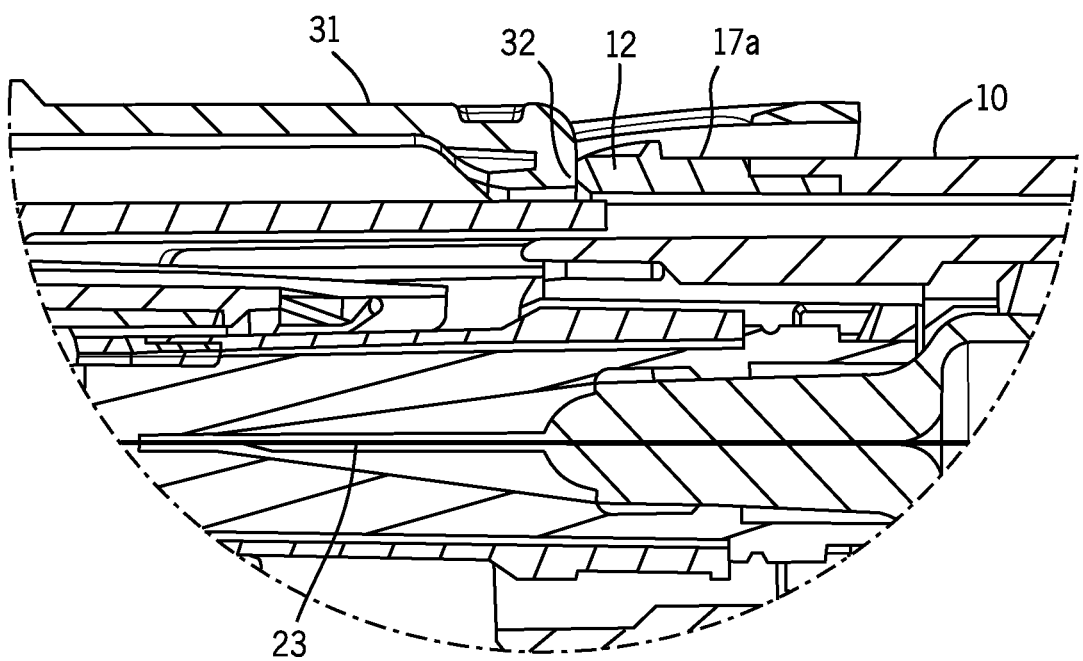

In addition to the features of the device from EP 2 745 866 A1, a construction of the injection device according to the invention has a mechanism 12, 32 that prevents the cover cap 30 from being remounted on the distal end of the housing 10. The mechanism 12, 32 or the injection device has an axial stop 12 and an axial mating stop 32. The axial stop 12 is formed by the housing 10, e.g., the sleeve-shaped section 17 of the housing 10. The axial stop 12 can be formed, for example, by or on the distal end of the housing 10. The axial mating stop 32 is formed by the cover cap 30, in particular, an outer sleeve 31. The outer sleeve 31 can be formed integrally with the cover cap 30. In the shown example, however, the outer sleeve 31 is fixed with a positive fit, for example, by an element connected by a snap-together connection to a cover cap base body 35. The cover cap base body 35 can be mounted, for example, on the housing 10, in particular, snapped together with the housing 10 or connected in some other way with a positive fit and/or non-positive fit. For example, the cover cap base body 35 can have an engagement element and the housing 10 can have an engagement mating element that engage with each other when the cover cap 30, in particular, the cover cap base body 35, is arranged or mounted on the housing 10. In an alternative construction (FIGS. 7a and 7b), the injection device can have a rotating sleeve 17a that is supported so that it can rotate, in particular, on and preferably relative to the housing 10 about the longitudinal axis of the injection device and on which the axial stop 12 is formed (FIG. 7b). In particular, the housing 10 can surround the rotating sleeve 17a. The rotating sleeve 17a is preferably axially fixed but could also be supported such that it is limitedly displaceable on the housing 10 along the longitudinal axis. It is preferred that the rotating sleeve 17a can be supported axially fixed on the housing 10 in the proximal direction. The cover cap 30 or a part or section of the cover cap 30 can slide on the rotating sleeve 17a during the removal of the cover cap 30 from the housing 10, and the rotating sleeve can 17a rotate about the longitudinal axis, whereby the axial stop 12 that is formed on the rotating sleeve is carried along accordingly with the rotating sleeve about the longitudinal axis (compare rotating sleeve 17a in FIGS. 7a and 7b), i.e., is rotated into a locking position (FIG. 7b). In the locking position, the axial stop 12 prevents the remounting of the cover cap 30 on the distal end of the housing 10, such that the axial stop 12 and the axial mating stop 32 contact each other like the mechanism 12, 32 that prevents the cover cap 30 from being remounted on the distal end of the housing 10 of the embodiment of FIGS. 1-6.

The cover cap 30, in particular, the outer sleeve 31, has an elastically pliant arm, for example, spring-like arm 34, which connects the outer sleeve 31 to the axial mating stop 32. The axial mating stop 32 has a resiliently-mounted arrangement due to the elastically pliant arm 34 approximately radial to the longitudinal axis L.

As can be seen from FIGS. 2a and 2b, the outer sleeve 31 can be displaced by means of the proximal end of the injection device. This is known as such from EP 2 745 866 A1. For instance, the outer sleeve 31 can slide along the injection device up to the cover cap 30 or the cover cap base body 35 until the outer sleeve 31 latches with the cover cap base body 35, such that the outer sleeve 31 is axially fixed, for example, along the longitudinal axis L, non-displaceable with the cover cap base body 35. Alternatively, the outer sleeve 31 could be connected to the cover cap base body 35 with a non-positive fit, for example, force fit or material bond, for example, by welding or bonding with the cover cap base body. Alternatively, the outer sleeve 31 can be displaced past the distal end of the injection device until it is connected, in particular, snapped together, with the cover cap base body 35. By pushing on the outer sleeve 31, a known device can be retrofitted with the mechanism that prevents the cover cap 30 from being remounted on the distal end of the housing 10.

FIGS. 1a and 1b show the outer sleeve 31 in a state mounted on the cover cap base body 35, wherein the cover cap base body 35 is mounted completely on the housing 10. In this starting state or mounted state of the injection device, the axial mating stop 32 engages in a recess 14 that extends inward from the outer periphery of the housing 10. In the shown example, the recess 14 is simultaneously a view window, through which the product container 20 can be inspected. The product container holder 45 can also have a recess or be made in the shown example from a transparent material, e.g., plastic, which allows the inspection of the product container 20 through the window-shaped recess 14. The distal end of the recess 14 has a transmission surface 13, wherein transmission surface is also understood to be a transmission edge on which an extension 33 that extends inward on the arm 34 and that forms the axial mating stop 32 can slide.

In the mounted state or starting state, the axial mating stop 32 is proximal to the axial stop 12, i.e., when the cover cap 30 is arranged on the housing 10. Due to the fact that the extension 33 is in the recess 14, the arm 34 is released from tension.

When the cover cap 30 is removed from the housing 10, the axial mating stop 32 is moved relative to the housing 10 in the distal direction, whereby the extension 33 or a transmission surface or transmission mating surface 36 pointing in the distal direction slides on the transmission surface 13, whereby the axial mating stop, in particular, the extension 33, is moved approximately radially outward, i.e., away from the longitudinal axis L. In this way, the elastically pliant arm 34 is tensioned (FIG. 3). The extension 33 now slides on the outer surface of the housing 10, in particular, along the section 17. The section 17 can have, for example, one or more steps that are traversed by the extension 33, in particular, such that the transmission surface or transmission mating surface 36 slides on the at least one step. As described further above, by removing the cover cap 30 from the housing 10, the needle protective cap 24 is simultaneously removed from the needle holding section of the product container 20. When the cover cap 30 is removed from the housing 10 (FIG. 5 and FIG. 7b), the axial mating stop 32 is moved by the arm 34 in a spring-like manner toward the longitudinal axis L, whereby it is in axial alignment with the axial stop 12.

If there is an attempt to reattach the cover cap 30 to the housing 10 or to remount it on the housing 10, the axial mating stop 32 that is in alignment with the axial stop 12 along the longitudinal axis L contacts the axial stop 12 (FIG. 6), whereby the cover cap 30 is prevented from being remounted on the housing 10.

In this way it is advantageously achieved that, on one hand, deformation of the locking means 37 due to a faulty remounting of the cover cap 30 on the housing 10 is prevented and, on the other hand, the faulty appearance that the needle 23 appears to still be sterile is prevented, even though the needle protective cap 24 has already released the injection needle 23 with respect to the surroundings.

LIST OF REFERENCE SYMBOLS

10 Housing
11 Propulsion element/plunger rod
12 Axial stop
13 Transmission or actuation surface
14 Recess
15 Stop
16 Second gap
17 Sleeve-shaped section
17a Rotating sleeve
20 Product container
21 Plunger
22 Product/medicine
23 Injection needle
24 Needle cover cap/needle protective sleeve
25 Product container section/syringe body
26 Finger flange
30 Cover cap
31 Element/outer sleeve
32 Axial mating stop
33 Extension
34 Arm
35 Cover cap base body
36 Transmission surface/transmission mating surface
37 Locking means
37a Contact surface
38 Engagement element
39 Inner sleeve of the cover cap base body
39a Holding surface
40 Release element
41 Sleeve-shaped section
42 First gap
45 Product container holder
L Longitudinal axis

What is claimed is:

1. An injection device for discharging a fluid product, comprising:

a) a housing with a longitudinal axis (L) and a product container arranged in the housing, the product container comprising a plunger, which can be displaced along the longitudinal axis (L) in a distal direction by means of a driving element for discharging the fluid product contained in the product container;

b) a sleeve-shaped release element that extends in a starting position past a distal end of the housing and can be moved relative to the housing in a proximal direction from the starting position into a release position for discharging the fluid product when a cover cap is removed from the housing, and is blocked against movement into the release position when the cover cap is arranged on the housing; and c) a mechanism that blocks the cover cap from being remounted on the distal end of the housing after the cover cap has been removed, wherein the mechanism comprises an axial stop and an axial mating stop, wherein the axial stop is formed by a rotating sleeve supported on the housing such that the rotating sleeve can rotate about the longitudinal axis (L) of the injection device and the axial mating stop is formed by the cover cap, wherein the cover cap or a part of the cover cap slides on the rotating sleeve during removal of the cover cap and rotates the rotating sleeve about the longitudinal axis (L), whereby the axial stop is rotated about the longitudinal axis (L) into a locking position, and wherein, in the locking position, the axial stop blocks the cover cap from being remounted on the distal end of the housing, in that the axial stop and axial mating stop contact each other upon an attempt to remount the cover cap on the distal end of the housing.

2. The injection device according to claim 1, wherein the product container comprises an injection needle non-detachably connected thereto, wherein the injection needle is surrounded by a needle protective cap that is detachably mounted on the product container.

3. The injection device according to claim 2, wherein the cover cap is connected to the needle protective cap such that removing the cover cap removes the needle protective cap from the product container.

4. The injection device according to claim 1, wherein the axial stop is resiliently-mounted, and when the cover cap is removed, the axial stop springs from a deflected position into the locking position.

5. The injection device according to claim 4, wherein the axial stop springs from the deflected position into the locking position by moving radially towards the longitudinal axis (L), or in a circumferential direction about the longitudinal axis (L), into the locking position.

6. The injection device according to claim 1, wherein the axial mating stop is resiliently-mounted, and when the cover cap is removed, the axial mating stop springs from a deflected position into the locking position.

7. The injection device according to claim 6, wherein the axial mating stop springs from the deflected position into the locking position by moving radially towards the longitudinal axis (L), or in a circumferential direction about the longitudinal axis (L), into the locking position.

8. The injection device according to claim 7, wherein the housing comprises an actuation surface that deflects the axial mating stop during the removal of the cover cap from the housing from a starting position into the deflected position.

9. The injection device according to claim 8, wherein the housing comprises, on an outer periphery, a recess in which an extension that forms the axial mating stop engages in the starting position, wherein a distal end of the recess forms the actuation surface.

10. The injection device according to claim 9, wherein the cover cap comprises a cover cap base body and an outer sleeve that is connected to the cover cap base body in a rotationally locked and axially fixed manner and forms the axial mating stop.

11. The injection device according to claim 10, wherein the axial mating stop is arranged proximal to the axial stop when the cover cap is arranged on the housing, and can be moved distally along the longitudinal axis (L) to the axial stop by removing the cover cap.

12. The injection device according to claim 1, wherein the release element comprises a resiliently-mounted locking means, wherein the locking means can be deflected by the cover cap into a locking position in which the locking means is opposite a stop formed by the injection device, wherein, in a release position that the locking means assumes, the locking means can be moved past the stop formed by the injection device when the cover cap is removed.

* * * * *